(12) United States Patent  (10) Patent No.: US 7,452,349 B2
Miyahara  (45) Date of Patent: Nov. 18, 2008

(54) MEDICAL CONNECTOR SYSTEM

(75) Inventor: Hiseyasu Miyahara, Aki-gun (JP)

(73) Assignee: JMS Co., Ltd., Hiroshima (JP)

( * ) Notice: Subject to any disclaimer, the term of this patent is extended or adjusted under 35 U.S.C. 154(b) by 399 days.

(21) Appl. No.: 10/565,953

(22) PCT Filed: Jul. 28, 2004

(86) PCT No.: PCT/JP2004/011114
§ 371 (c)(1),
(2), (4) Date: Jan. 26, 2006

(87) PCT Pub. No.: WO2005/011798
PCT Pub. Date: Feb. 10, 2005

(65) Prior Publication Data
US 2006/0189961 A1   Aug. 24, 2006

(30) Foreign Application Priority Data
Jul. 31, 2003   (JP)   ............................. 2003-284160

(51) Int. Cl.
*A61M 5/32* (2006.01)
(52) U.S. Cl. ...................... 604/415; 604/905
(58) Field of Classification Search ................. 285/402, 285/376; 604/415, 905
See application file for complete search history.

(56) References Cited
U.S. PATENT DOCUMENTS

| 4,511,359 A | 4/1985 | Vaillancourt |
| 4,610,469 A | 9/1986 | Wolff-Mooij |
| 4,810,242 A | 3/1989 | Rogers |
| 5,792,120 A | 8/1998 | Menyhay |

(Continued)

FOREIGN PATENT DOCUMENTS

EP   1 331 020   1/2003

(Continued)

*Primary Examiner*—David E Bochna
(74) *Attorney, Agent, or Firm*—Hamre, Schumann, Mueller & Larson, P.C.

(57) ABSTRACT

There are provided a male type connector (1), a protective cap (2), an inner cap (3) that supports a disinfectant-impregnated member therein and is retained in the protective cap, and a female type connector (4) in which an inner cylinder is fixed at an end of an outer cylinder, the inner cylinder including an internal end portion located inside the outer cylinder and an exposed external end portion. The inner cap includes engaging legs at each of which an engaging convexity is formed. A front end portion of the male type connector allows the engaging convexities at the engaging legs to engage therewith from inside. An inner cap retaining portion is formed on an inner wall surface of the protective cap, and a force exerted by the engagement between the inner cap and the male type connector is larger than a force exerted by the inner cap retaining portion to retain the inner cap. When the protective cap with the inner cap retained therein is fitted with the male type connector, and then is removed from the male type connector, the inner cap is retained in the male type connector and is detached from the protective cap. When the male type connector is connected with the female type connector, the internal end portion of the inner cylinder penetrates through the disinfectant-impregnated member, so that a channel is opened. When the connecting and detaching are repeated, the bacterial contamination can be reduced with a simple operation.

8 Claims, 8 Drawing Sheets

U.S. PATENT DOCUMENTS

| | | | |
|---|---|---|---|
| 6,911,025 B2 * | 6/2005 | Miyahara | 604/415 |
| 7,083,605 B2 * | 8/2006 | Miyahara | 604/415 |
| 2003/0144647 A1 | 7/2003 | Miyahara | |

FOREIGN PATENT DOCUMENTS

| | | |
|---|---|---|
| JP | 5-031178 | 2/1993 |
| JP | 6-312014 | 11/1994 |
| JP | 2002-345952 | 12/2002 |

* cited by examiner

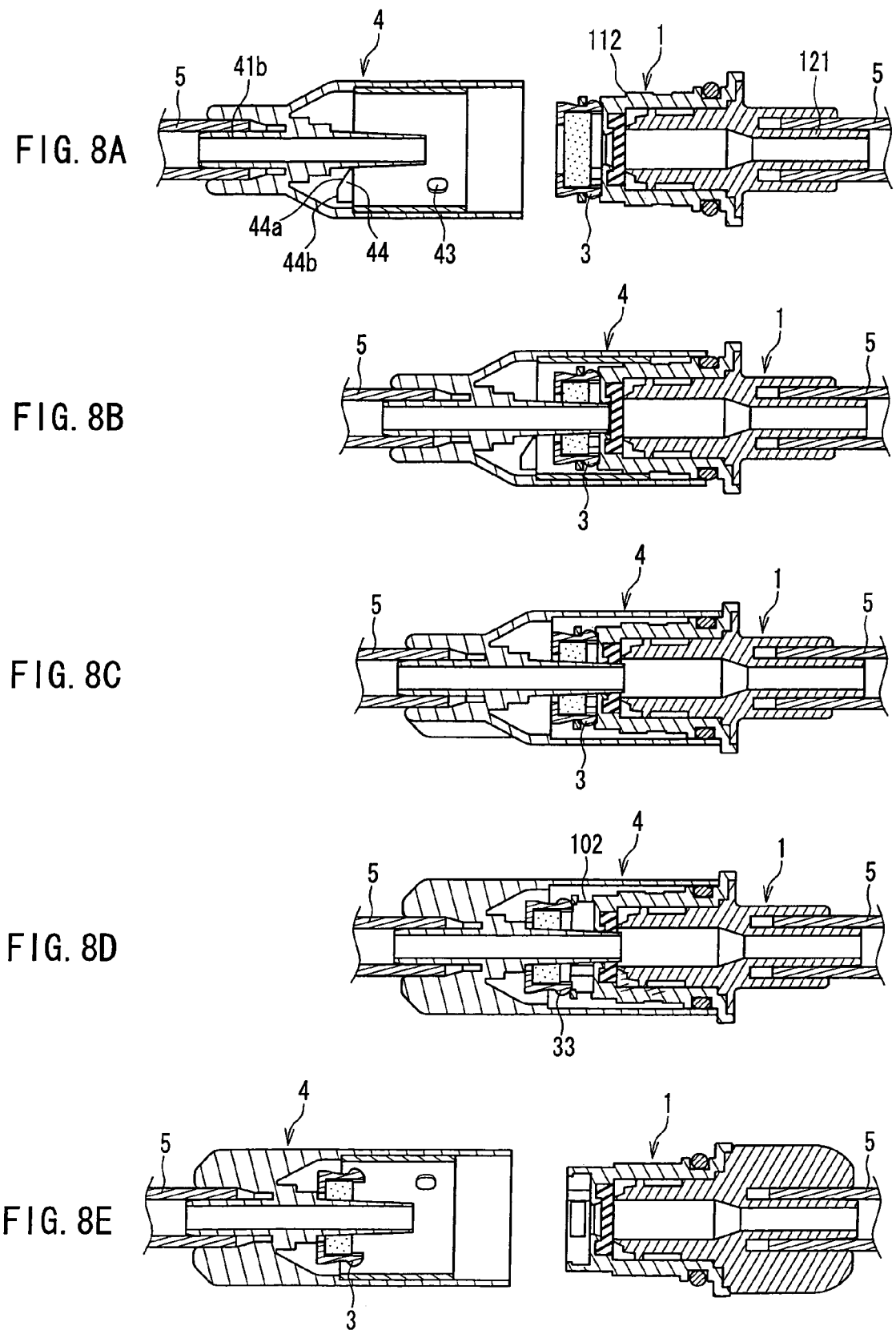

MEDICAL CONNECTOR SYSTEM

TECHNICAL FIELD

The present invention relates to a medical connector system for connecting a tube or the like that forms a channel for a solution for medical use, for example. In particular, the present invention relates to a medical connector system provided with a function of securely disinfecting a connecting portion with a simple operation when the connecting and detaching are repeated.

BACKGROUND ART

Known examples of medical connectors include a connector for connecting a patient side transfer tube (extension tube) with a peritoneal dialysis unit when a dialysis solution for peritoneal dialysis is exchanged. Peritoneal dialysis is a medical treatment method in which a dialysis solution is stored in a patient's abdominal cavity by way of a peritoneal catheter that is implanted surgically in the patient's abdominal cavity beforehand, so that impurities accumulated in the body are filtered using capillary vessels in the peritoneum. The patient undertakes daily activities while a transfer tube (extension tube), which is used continuously for a half year, is connected to the end of the catheter. Then, the patient himself/herself connects a bag containing a dialysis solution with a front end of the transfer tube four times per day to exchange the dialysis solution in the abdominal cavity.

The most serious problem to be addressed for carrying out the peritoneal dialysis is bacteria in the air or attached to the skin inadvertently entering into the abdominal cavity with the dialysis solution during the operation of exchanging the dialysis solution, which is required four times per day. If bacteria enter into the abdominal cavity, these bacteria cause inflammation of the peritoneum to develop peritonitis.

Thus, in the peritoneal dialysis, it is important, when the dialysis solution is exchanged, to reduce the bacterial contamination of a connector that connects a transfer tube and a peritoneal dialysis unit. Conventionally, products for connecting tubes by melting with a heated copper plate or for disinfecting a connecting portion with ultraviolet rays are available commercially for preventing the bacterial contamination. However, since these products necessarily require units dedicated to the products, a patient always has to carry the unit. Moreover, in the event of problems with the unit, serious problems might occur.

Meanwhile, as for connecting members that do not require the units and can prevent the bacterial contamination, various structures have been examined. Examples of those ideas are a structure using a septum, which is pushed open to realize the fitting for connection and a structure where fitting is realized by breaking a film covering a connecting portion (see, for example, U.S. Pat. No. 4,610,469 A and JP 6(1994)-312014 A).

However, all of those connectors known conventionally have problems that their mechanism is complicated, their size is large, and the required functions cannot be obtained sufficiently, and therefore none of them have been put into practical use. In particular, there is no connector that is constructed by paying sufficient attention to the structure for preventing the bacterial contamination when the connecting and detaching are repeated.

These problems are not peculiar to connectors that connect a tube for peritoneal dialysis but are common to connectors for use in places where the connection between channels for a solution, such as a usual infusion solution, is required.

DISCLOSURE OF INVENTION

It is an object of the present invention to provide a medical connector system that is capable of reducing the bacterial contamination with a simple operation when a channel for a solution is connected.

A medical connector system according to the present invention includes: a male type connector including a tube connecting portion at a rear end portion of the male type connector; a protective cap having a substantially cylindrical shape with a closed end and being capable of connecting and disconnecting with/from a front end side of the male type connector; an inner cap including an annular portion that supports a disinfectant-impregnated member in the annular portion, the inner cap being retained inside the protective cap in an initial state; and a female type connector having a double-cylinder structure in which an inner cylinder is fixed at one end portion of an outer cylinder. The inner cylinder includes an internal end portion located inside the outer cylinder and an external end portion that is exposed outside the outer cylinder and is capable of connecting with a tube.

The inner cap includes a plurality of engaging legs extending from the annular portion in a direction along an axis of the annular portion. An engaging convexity is formed at an outside of a front end portion of each of the engaging legs, the front end portion of the male type connector has a cylindrical shape and includes engaging concavities so as to allow the engaging convexities at the engaging legs to engage with the engaging concavities from inside, and an inner cap retaining portion is formed on an inner wall surface of the protective cap. A force exerted by the engagement between the engaging convexity of the inner cap and the engaging concavity of the male type connector is larger than a force exerted by the inner cap retaining portion to retain the inner cap.

When the protective cap with the inner cap retained in the protective cap is fitted with the male type connector, the engaging convexities at the engaging legs engage with the engaging concavities of the male type connector. When the protective cap is removed from the male type connector, the inner cap is retained at the front end of the male type connector and is detached from the protective cap. When the male type connector with the inner cap retained in the male type connector is connected with the female type connector, the internal end portion of the inner cylinder penetrates through the disinfectant-impregnated member, so that a channel is opened.

BRIEF DESCRIPTION OF DRAWINGS

FIGS. 8A to 8E are cross-sectional views for explaining the operation for connecting and disconnecting the male type connector with/from the female type connector constituting the medical connector system.

DESCRIPTION OF THE INVENTION

Figure 1A:
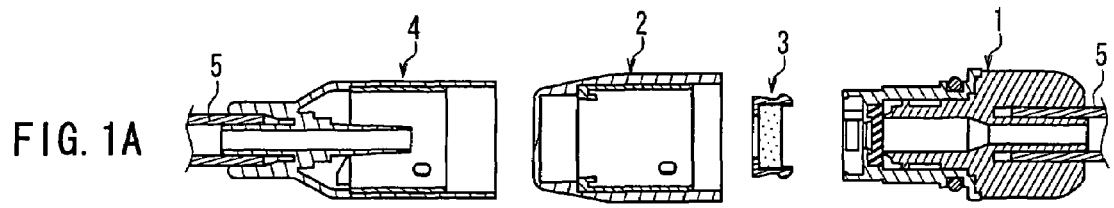
FIG. 1A is a front cross-sectional view showing respective elements constituting a medical connector system according to an embodiment of the present invention.

According to the medical connector system of the present invention having the above configuration, the disinfectant-impregnated member in the inner cap can prevent the bacterial contamination of the front end portion of the male type connector. Further, every time the protective cap is exchanged, the inner cap is exchanged into a new one, and therefore this system can be disinfected by a new disinfectant-impregnated member without a complicated procedure.

In the medical connector system according to the present invention, preferably, the female type connector includes an inner cap retaining portion, and when the connection between the male type connector and the female type connector is released, the inner cap is retained inside the female type connector by the inner cap retaining portion and is detached from the front end of the male type connector.

Preferably, the male type connector includes a septum member at the front end portion of the male type connector for shielding an inner cavity, and when the male type connector with the inner cap retained at the front end of the male type connector is connected with the female type connector, the internal end portion of the inner cylinder penetrates through the disinfectant-impregnated member in the inner cap and the septum member of the male type connector, so that a channel is opened.

Preferably, on an outer surface of the male type connector, a circumferential step portion extending in a circumferential direction is formed so that a diameter at the front end side of the male type connector is smaller than that at a base end side, and a guide groove is formed so as to extend from the circumferential step portion toward the base end, the guide groove including an inclined portion that is inclined with respect to an axis of the male type connector. On the inner wall surface close to an opening end portion of the protective cap, a guide protrusion is formed. When the male type connector is inserted from an opening of the protective cap with the guide protrusion of the protective cap facing the guide groove of the male type connector, and then the protective cap and the male type connector are rotated while being urged axially toward each other, the guide protrusion slides along the guide groove, so that the male type connector is pulled into an inside of the protective cap by a driving force resulting from a screw action by the inclined portion of the guide groove, and the engaging convexities of the inner cap engage with the engaging concavities of the male type connector.

Preferably, the male type connector includes a blocking protrusion on an inner circumferential surface of the front end portion of the male type connector, which is capable of contacting with a side face portion of the engaging leg of the inner cap when the inner cap is fitted with the male type connector, the outer cylinder of the female type connector includes a guide protrusion formed on an inner wall surface close to an open end portion of the outer cylinder and a guide step portion including an inclined portion that is inclined with respect to an axis of the female type connector, and the inner cap includes protrusions on an outer circumferential surface of the annular portion. When the male type connector with the inner cap retained in the male type connector is inserted from an opening of the female type connector with the guide protrusion of the outer cylinder facing the guide groove of the male type connector, and then the female type connector and the male type connector are rotated while being urged axially toward each other, the guide protrusion slides along the guide groove, so that the male type connector is pulled into an inside of the female type connector by a driving force resulting from a screw action by the inclined portion of the guide groove. At the same time the protrusions of the annular portion slide along the inclined portion of the guide step portion of the female type connector while rotation of the engaging legs of the inner cap relative to the male type connector is blocked by the blocking protrusion of the male type connector, so that a force in the axis direction acts on the inner cap so as to separate the inner cap from the male type connector, resulting in release of the engagement between the inner cap and the male type connector, and further the inner cap assumes a state of being retained by the inner cap retaining portion of the outer cylinder.

Preferably, the inner cap retaining portion of the female type connector is configured with a horizontal step portion provided continuously at an inside of the inclined portion of the guide step portion, and when the protrusions of the annular portion of the inner cap contact with the horizontal step portion, the inner cap is prevented from moving in the axis direction toward the opening of the outer cylinder so as to be retained in the female type connector.

Preferably, the inner cap retaining portion of the female type connector is configured by setting dimensions of constituting elements so that portions of the inner wall of the outer cylinder contact with the outer circumferential surface of the annular portion of the inner cap or so that portions of an outer wall of the internal end portion of the inner cylinder contact with an inner circumferential surface of the annular portion of the inner cap, whereby the inner cap is retained by the thus exerted frictional force.

A protective cap assembled member used in the medical connector system having the above configuration includes: the protective cap having a substantially cylindrical shape with a closed end; and the inner cap retained at an inside of the protective cap and including an annular portion with a disinfectant-impregnated member supported in the annular portion. On an inner wall surface of the protective cap, an inner cap retaining portion for retaining the inner cap is formed. The inner cap includes a plurality of engaging legs extending from a circumferential edge portion of the annular portion in a direction along an axis of the annular portion, and an engaging convexity is formed at a front end of each of the engaging legs so as to protrude outward. The inner cap is retained in the inner cap retaining portion so that the front ends of the engaging legs are directed toward an opening of the protective cap.

The following describes specifically a configuration of a medical connector system according to an embodiment of the present invention with reference to FIGS. 1A to 1G, FIGS. 2A to 2C, FIGS. 3A and 3B, FIGS. 4A to 4C, FIGS. 5A to 5C, and FIGS. 6A and 6B. The description of the present embodiment is given taking as an application example connectors for connecting tubes in peritoneal dialysis.

As indicated by an exploded view of FIG. 1A, this medical connector system includes a male type connector 1, a protective cap 2, an inner cap 3, and a female type connector 4. The male type connector 1 is connected to a front end of an extension tube 5 that leads to a peritoneal catheter implanted in a patient's abdominal cavity, for example. The female type connector 4 is connected to an extension tube 5 as a front end of a circuit in a peritoneal dialysis unit, such as a twin bag, BF, and APD, for example. The inner cap 3 initially is supplied in a state of being retained in the protective cap 2 as shown on the right side of FIG. 1B. The inner cap 3 is equipped with a disinfectant-impregnated member, such as a disinfecting sponge impregnated with a disinfectant, which will be described later. The outline of a function of each of the elements constituting this medical connector system will be described below with reference to FIGS. 1B to 1G.

Figure 1B:
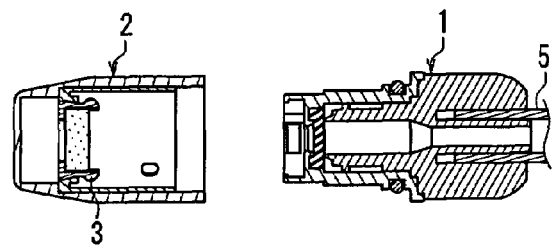
FIGS. 1B to 1G are front cross-sectional views showing the operation of the medical connector system.
Figure 1C:
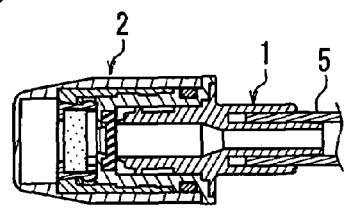

The protective cap 2 is fitted with the male type connector 1 when the male type connector 1 is not connected with the female type connector 4, for protecting a front end of the connector. For this purpose, as shown in FIG. 1B, the protective cap 2 that retains the inner cap 3 therein is opposed to the male type connector 1, and they are fitted with each other as shown in FIG. 1C. In this state, the disinfectant-impregnated member provided in the inner cap 3 covers the front end portion of the male type connector 1 so as to perform a disinfecting function.

Figure 1D:
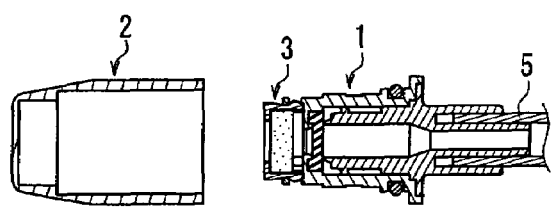
Figure 1E:
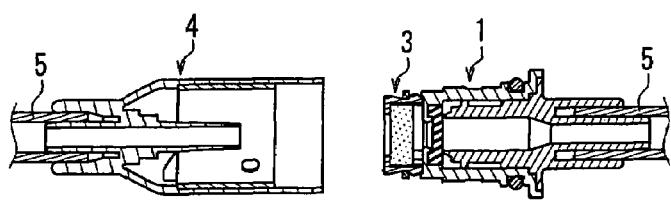
Figure 1F:
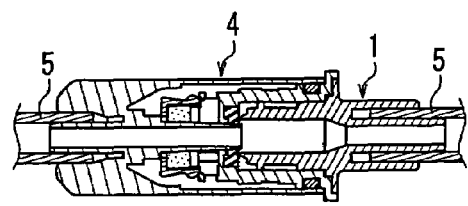
Figure 1G:
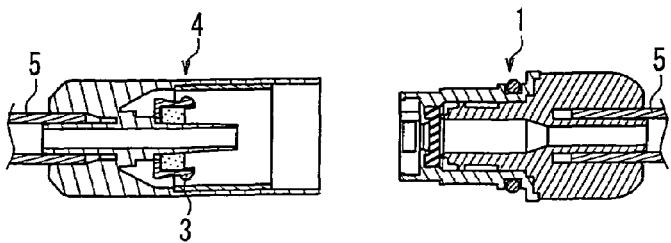

When the male type connector 1 is to be connected with the female type connector 4, firstly, the protective cap 2 is detached and removed from the male type connector 1. In this detachment operation, the inner cap 3 is transferred from the protective cap 2 to the male type connector 1 as shown in FIG. 1D. As shown in FIG. 1E, the female type connector 4 is opposed to the male type connector 1 and, as shown in FIG. 1F, is connected with the male type connector 1, thus forming a channel. As shown in FIG. 1G, when the connection between the male type connector 1 and the female type connector 4 is released, the inner cap 3 finally is transferred to the inside of the female type connector 4 in accordance with the operation that will be described later, and is discarded together with the female type connector 4.

Figure 2A:
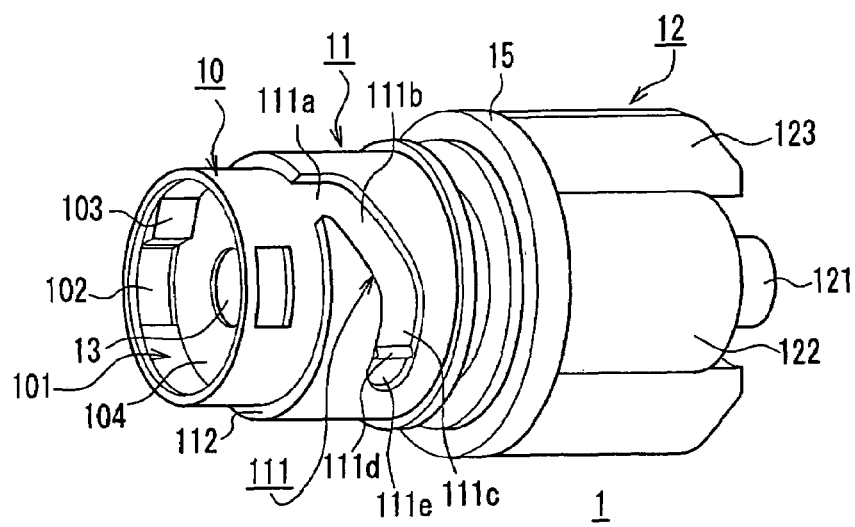
FIG. 2A is a perspective view showing a male type connector constituting the medical connector system.
Figure 2B:
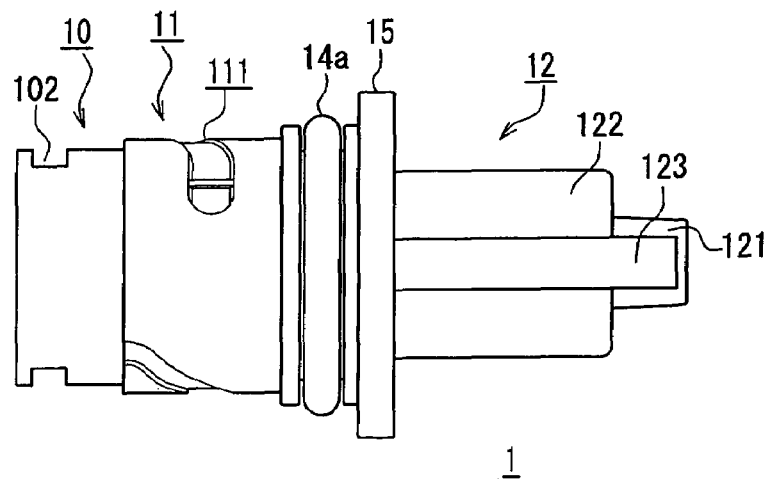
FIG. 2B is a front view of the same.
Figure 2C:
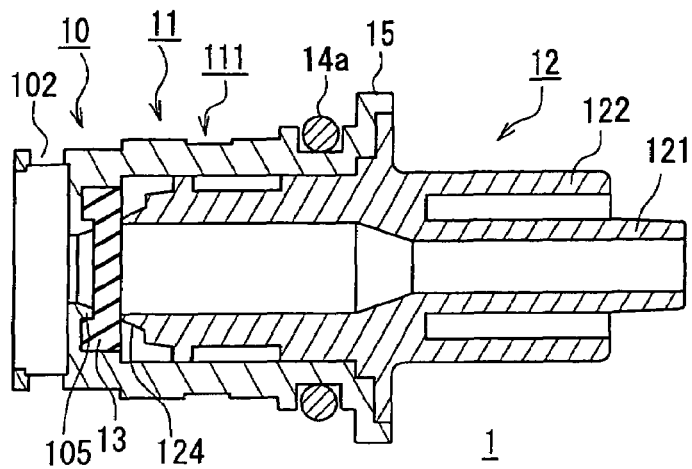
FIG. 2C is a cross-sectional view of the same.

Each of the above constituting elements will be described below in detail. Firstly, the male type connector 1 will be described with reference to FIGS. 2A to 2C. FIG. 2A is a perspective view of the male type connector 1, FIG. 2B is a front view of the same, and FIG. 2C is a cross-sectional view of the same.

A main body of the male type connector 1 is made of resin, has a substantially cylindrical shape, and includes a front end portion 10, a guide portion 11 in the middle, and a base end portion 12 on a rear end side. As shown in FIG. 2C, an inner cavity is formed so as to penetrate the front end portion 10, the guide portion 11, and the base end portion 12. FIGS. 2B and 2C illustrate the male type connector 1 in a state rotated around the axis of the main body by 90° from the state shown in FIG. 2A.

A septum member 13 such as a rubber septum (with a slit) is fitted with the front end portion 10 so as to shield and protect a channel formed by the inner cavity and ensure liquid-tightness. Note here that the septum 13 is effective for ensuring liquid-tightness in the connecting state with the female type connector 4, but this element is not essential. Therefore, the liquid-tight seal may be ensured by other methods. At a boundary portion between the guide portion 11 and the base end portion 12, an annular groove 14 and a flange 15 are formed, and an O ring 14a is mounted on the annular groove 14 (not illustrated in FIG. 2A).

In the front end portion 10, a concavity 101 is formed so as to hold the inner cap 3 therein. A pair of engaging holes 102 are provided on a side wall of the front end portion 10. These engaging holes 102 are used to lock the inner cap 3. This operation will be described later. Blocking protrusions 103 are formed adjacent to the respective engaging holes 102.

A guide groove 111 is formed on an outer circumferential surface of the guide portion 11. A pair of the guide grooves 111 are provided symmetrically with respect to the axis of the main body, and one of the guide grooves 111 is located on the reverse side of FIG. 2A. The pair of guide grooves 111 are not necessarily required, and only one guide groove may function sufficiently. The guide groove 111 includes an axis direction portion 111a extending in the axis direction of the main body, an inclined portion 111b that is inclined, and a circumferential portion 111c extending along the circumferential direction. In the circumferential portion 111c, a locking convex stripe 111d is formed so as to separate a trailing end portion 111e of the guide groove 111. The front end portion 10 has a smaller outer diameter than that of the guide portion 11, so that an annular step portion 112 extending in the circumferential direction is formed on an outer surface of a boundary between the front end portion 10 and the guide portion 11. A front end of the axis direction portion 111a of the guide groove 111 leads to the annular step portion 112.

In the base end portion 12, a tube-shaped tube connecting portion 121 is formed for the connection with the extension tube (not illustrated). A protective cylinder 122 is formed around the tube connecting portion 121, and a knob 123 is provided on either side of the protective cylinder 122. The knob 123 is used for supporting firmly when the male type connector 1 is rotated.

In the present embodiment, as shown in FIG. 2C, the base end portion 12 is formed separately from the front end portion 10 and the guide portion 11 with a part thereof being fitted with an inner cavity of the guide portion 11. This structure constitutes means for supporting the septum 13 in the front end portion 10. More specifically, the septum 13 is interposed between a flange-shaped septum supporting portion 104 formed in an inner cavity of the front end portion 10 and a pressing end 124 of the base end portion 12. A hook portion 105 is formed on an inner circumferential edge of the septum supporting portion 104 for engaging with a step portion formed on a surface of the septum 13 to suppress the deformation of the septum 13. The septum supporting portion 104 preferably has this structure for convenience in resin molding, but other structures also may be adopted for supporting the septum 13.

Figure 3A:
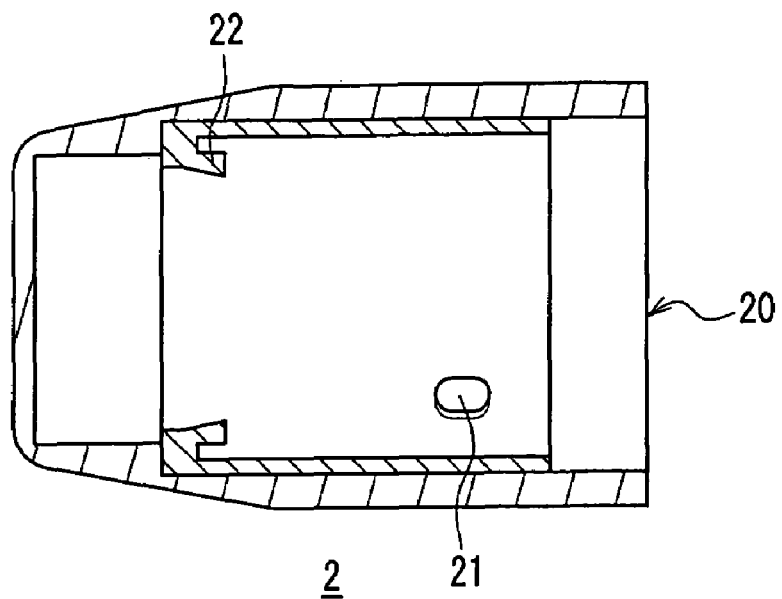
FIG. 3A is a cross-sectional view showing a protective cap constituting the medical connector system.
Figure 3B:
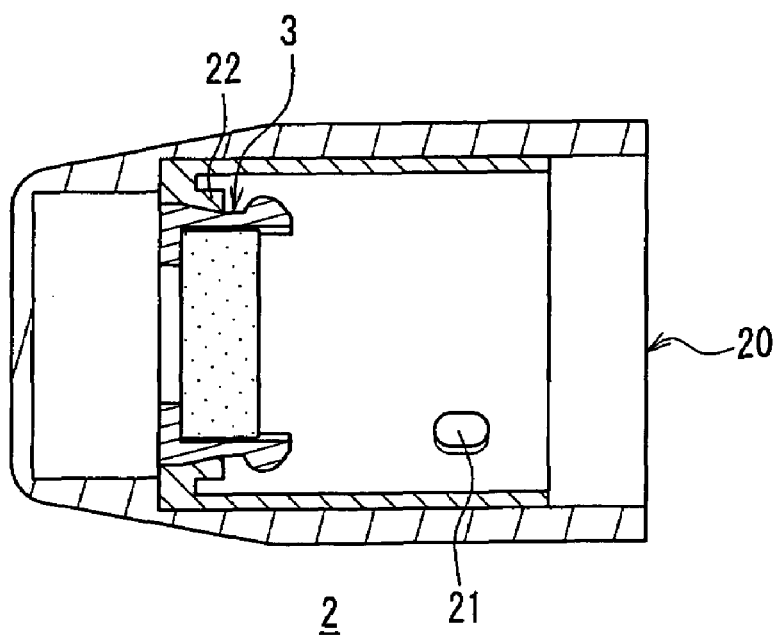
FIG. 3B is a cross-sectional view showing a state where an inner cap is retained in the protective cap.

Next, the protective cap 2 will be described with reference to the cross-sectional views shown in FIGS. 3A and 3B. FIG. 3A shows a state where the inner cap is not retained, and FIG. 3B shows a state where the inner cap is retained. The protective cap 2 is made of resin and has a hollow structure with a substantially cylindrical shape whose front end is closed. On an inner wall surface close to an opening 20 of the protective cap 2, a guide protrusion 21 is formed. Although a pair of the guide protrusions 21 are provided symmetrically, only one of them is illustrated in the figures. On an inner circumferential surface on the closed end side of the protective cap 2, a retaining detent 22 is formed, where the inner cap 3 is retained as shown in FIG. 3B.

When the male type connector 1 is inserted from the opening 20 of the protective cap 2, the guide protrusion 21 engages with the guide groove 111 in the male type connector 1, and a guiding function for adjusting a mutual positional relationship between the protective cap 2 and the male type connector 1 is obtained by the engagement. This operation will be described later.

Figure 4A:
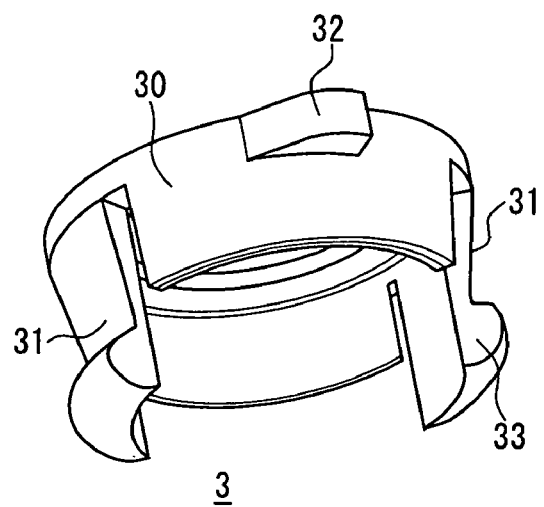
FIG. 4A is a perspective view showing the inner cap constituting the medical connector system.
Figure 4B:
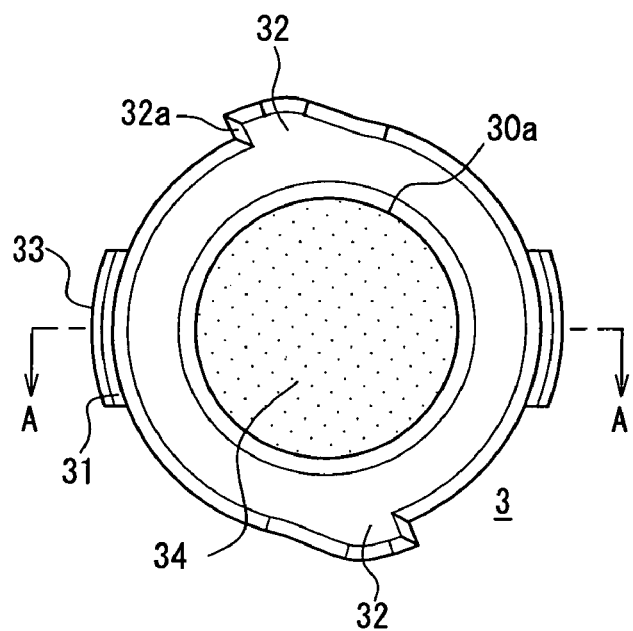
FIG. 4B is a plan view of the same.
Figure 4C:
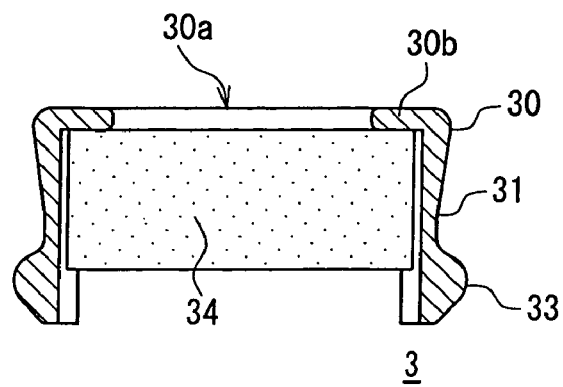
FIG. 4C is a cross-sectional view of the same.

Next, the inner cap 3 will be described with reference to FIGS. 4A to 4C. FIG. 4A is a perspective view of the inner cap 3, FIG. 4B is a front view of the same, and FIG. 4C is a cross-sectional view of the same taken along a line A-A in FIG. 4B. The inner cap 3 is made of resin and includes an annular portion 30 and two engaging legs 31. On an outer circumferential surface of the annular portion 30, a pair of protrusions 32 are formed between the pair of engaging legs 31 in the circumferential direction. A step portion 32a is formed on one side of the protrusion 32. At a front end of each of the engaging legs 31, an engaging convexity 33 is formed so as to protrude outward.

Inside the annular portion 30, a disinfecting sponge 34 is installed (illustrated only in FIGS. 4B and 4C and not illustrated in FIG. 4A). The disinfecting sponge 34 is arranged so as to shield an opening 30a of the annular portion 30 and is fixed to a flange 30b of the annular portion 30 by ultrasonic welding, for example. A straight-line or cross-shaped slit (not illustrated) is provided in the disinfecting sponge 34 so that an internal end portion 41b of the female type connector 4, which will be described later, can penetrate therethrough, and the disinfecting sponge 34 is impregnated with a disinfectant such as povidone iodine.

As previously described, the inner cap 3 initially is held in the protective cap 2 as shown in FIG. 3B. The annular portion 30 of the inner cap 3 is held tight by the retaining detent 22, so that the inner cap 3 is retained by the frictional engagement therebetween. When the protective cap 2 is fitted with the male type connector 1, the engaging convexities 33 of the engaging legs 31 slide on an inner circumferential surface of the front end portion 10 of the male type connector 1 while the protective cap 2 and the male type connector 1 are rotated relative to each other. In order to prevent the retaining of the inner cap 3 by the retaining detent 22 of the protective cap 2 from being released by the frictional force exerted when the engaging convexities 33 slide on the inner circumferential surface of the front end portion 10, a force to retain the inner cap 3 is required to be set properly. Preferably, a rotation-blocking portion is provided in the protective cap 2 so as to block the rotation of the inner cap 3 by contacting with the step portions 32a formed of the protrusions 32 of the inner cap 3.

Figure 5A:
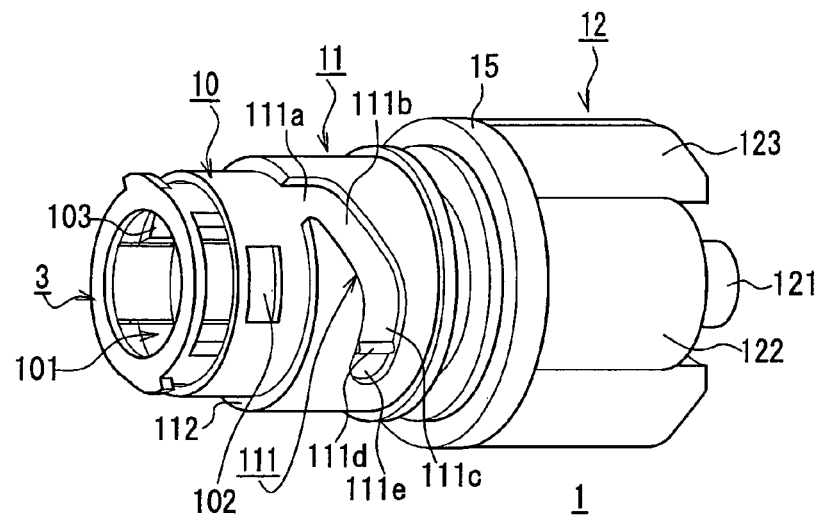
FIG. 5A is a cross-sectional view showing a state where the inner cap is fitted with the male type connector constituting the medical connector system.
Figure 5B:
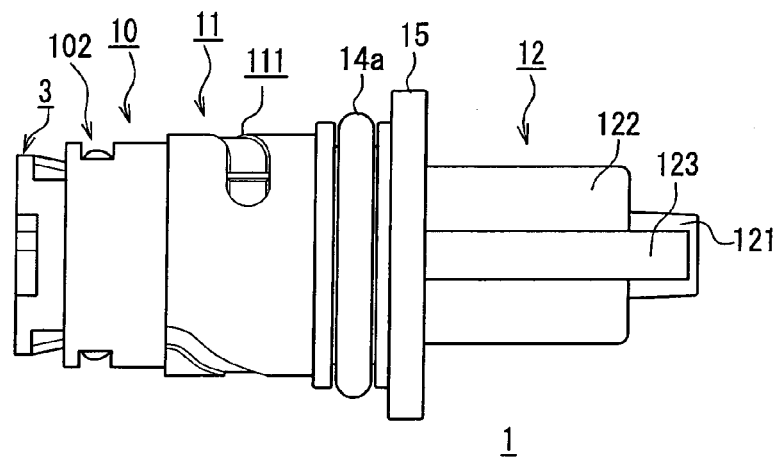
FIG. 5B is a front view of the same.
Figure 5C:
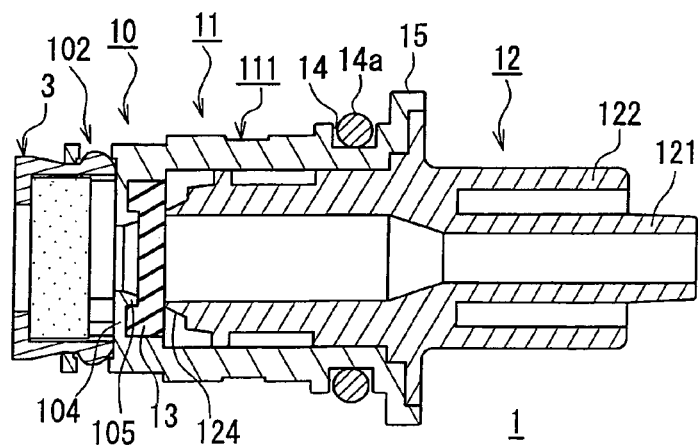
FIG. 5C is a cross-sectional view of the same.

FIGS. 5A to 5C show a state where the inner cap 3 is retained in the front end portion 10 of the male type connector 1. In a state where the protective cap 2 is fitted with the male type connector 1, the engaging convexities 33 of the engaging legs 31 of the inner cap 3 engage with the engaging holes 102 in the front end portion 10 of the male type connector 1. This engagement allows the inner cap 3 to be retained in the front end portion 10. The engaging holes 102 are not necessarily through holes, and recessed portions may be available that are formed so that the engaging convexities 33 of the inner cap 3 can engage therewith.

As stated above, the inner cap 3 is retained in the protective cap 2 by the frictional engagement with the retaining detent 22 of the protective cap 2. Further, the engagement between the engaging holes 102 of the male type connector 1 and the engaging convexities 33 of the inner cap 3 allows the inner cap 3 to be retained in the male type connector 1. A force exerted by the engaging holes 102 of the male type connector 1 to retain the inner cap 3 is set to be larger than a force exerted by the retaining detent 22 of the protective cap 2 to retain the inner cap 3.

Figure 6A:
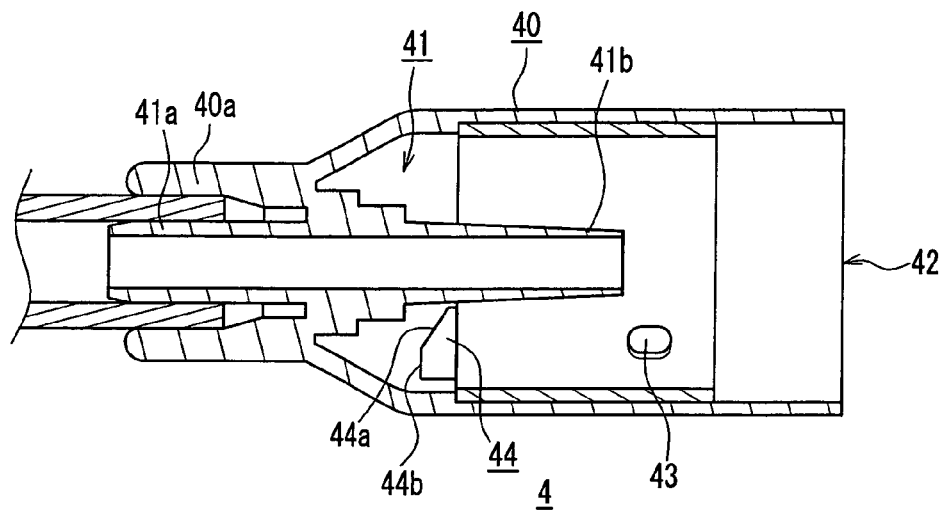
FIG. 6A is a cross-sectional view showing a female type connector constituting the medical connector system.
Figure 6B:
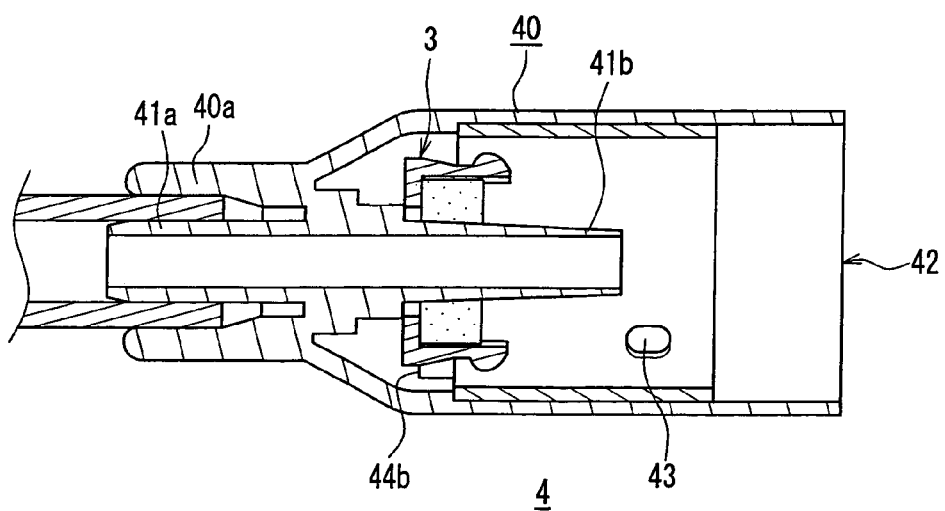
FIG. 6B is a cross-sectional view showing a state where the inner cap is retained in the female type connector.

Next, the female type connector 4 will be described with reference to the cross-sectional views shown in FIGS. 6A and 6B. FIG. 6A shows a state where the inner cap is not retained, and FIG. 6B shows a state where the inner cap is retained.

The female type connector 4 has a double-cylinder structure including an outer cylinder 40 and an inner cylinder 41 made of resin, the inner cylinder 41 being fixed at one end portion of the outer cylinder 40. The outer cylinder 40 has an opening 42 on the opposite side to the side where the inner cylinder 41 is fixed, to define a front end portion of the female type connector 4. The inner cylinder 41 includes an external end portion 41a exposed outside the outer cylinder 40 and an internal end portion 41b located inside the outer cylinder 40. The external end portion 41a is capable of connecting with the tube as a front end of a circuit in a peritoneal dialysis unit, for example. The external end portion 41a is surrounded by a protective cylinder 40a, which is formed of protruding one end portion of the outer cylinder 40. On either side of an outer circumferential surface of the protective cylinder 40a, a knob is formed in the same manner as the knob 123 in the male type connector 1, which is not illustrated in FIGS. 6A and 6B. When the female type connector 4 is connected with the male type connector 1, the internal end portion 41b pushes and expands the slit in the disinfecting sponge 34 in the inner cap 3 fitted at the front end of the male type connector 1 and the slit in the rubber septum 13 supported in the front end portion 10 so as to penetrate through the male type connector 1, whereby the channel is opened.

On an inner wall close to the opening 42 of the outer cylinder 40, a guide protrusion 43 is formed. The guide protrusion 43 has the same shape and function as those of the guide protrusion 21 formed in the protective cap 2. On an inner wall at an inside of the outer cylinder 40, a guide step portion 44 is formed. The guide step portion 44 includes an inclined portion 44a inclined with respect to the axis direction of the outer cylinder 40, and a horizontal step portion 44b that is orthogonal to the axis direction. The horizontal step portion 44b functions as means for retaining the inner cap 3 at the inside of the outer cylinder 40. That is, when the inner cap 3 is pushed into the inside of the outer cylinder 40, and the protrusions 32 contact with the horizontal step portion 44b, the inner cap 3 is retained in this state. The operation for the same will be described later.

Means for retaining the inner cap 3 may be configured so that portions of an inner wall of the inside of the outer cylinder 40 contact with an outer circumferential surface of the annular portion 30 of the inner cap 3, whereby the inner cap 3 is retained by the thus exerted frictional force. Alternatively, an outer circumferential surface of the inner cylinder 41 may be configured so as to contact with an inner circumferential surface of the flange 30b of the inner cap 3, whereby the inner cap 3 is retained by the thus exerted frictional force.

In FIGS. 6A and 6B, the guide protrusion 43 and the guide step portion 44 are formed on a member separated from a wall material of the outer cylinder 40. Although this structure may be preferable for convenience in resin molding, the guide protrusion 43 and the guide step portion 44 may be formed on the wall material of the outer cylinder 40 integrally. Further, preferably, in a state before use, a breakable film (not illustrated) is provided at a front end portion of the outer cylinder 40 of the female type connector 4 for protecting the inner cylinder and the channel in the female type connector 4 until immediately before use.

Next, the operation of the medical connector system having the above configuration will be described below.

Firstly, the operation for fitting the protective cap 2 with the male type connector 1 and further detaching the protective cap 2 from the male type connector 1 will be described with reference to FIGS. 7A to 7E. For the details of the structures of the male type connector 1, the protective cap 2, and the inner cap 3, see FIGS. 2A to 2C, FIGS. 3A and 3B, and FIGS. 4A to 4C, respectively.

Figure 7A:
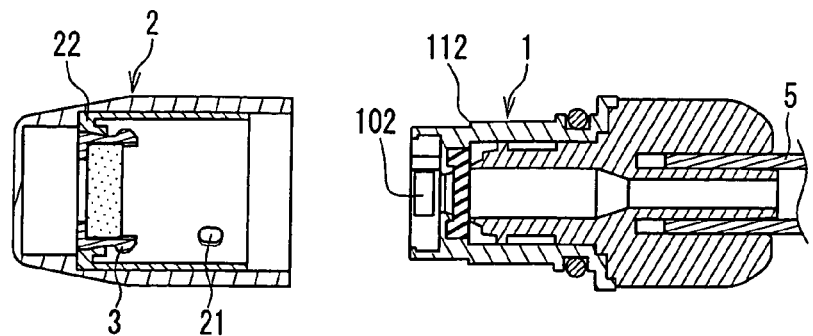
FIGS. 7A to 7E are cross-sectional views for explaining the operation for fitting and detaching the protective cap with/from the male type connector constituting the medical connector system.
Figure 7B:
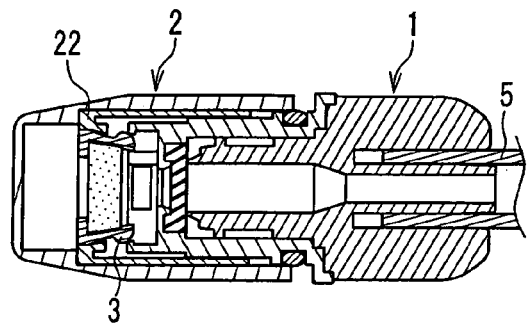
Figure 7C:
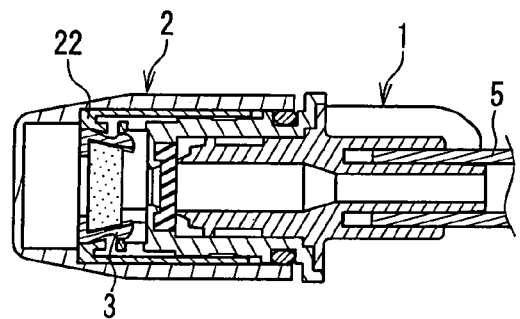
Figure 7D:
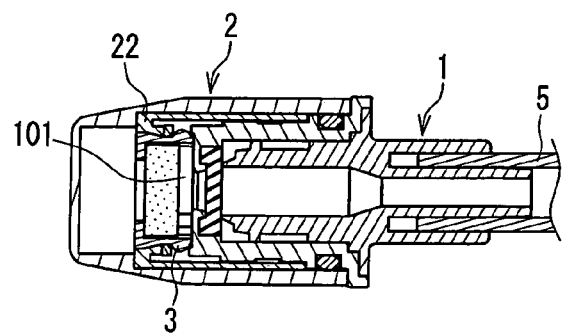
Figure 7E:
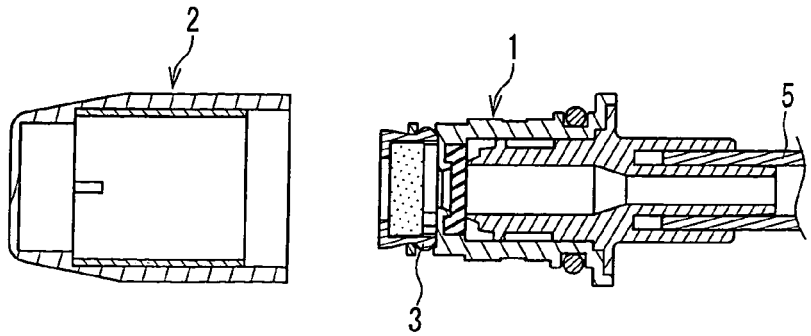

FIGS. 7A to 7D show states at respective angular positions during an operation in which the male type connector 1 is rotated while the protective cap 2 is fixed. The male type connector 1 in FIG. 7A is at the angular position in FIG. 2A. From this state, by rotating the male type connector 1 by 90° clockwise when viewed from the base end side, the state of FIG. 7D is obtained. FIG. 7E shows a state where the protective cap 2 is rotated by 90° from the state shown in FIG. 7D.

To begin with, as shown in FIG. 7A, the protective cap 2 that retains the inner cap 3 therein is opposed to the male type connector 1, and then as shown in FIG. 7B, the male type connector 1 is inserted into the protective cap 2. During this operation, the guide protrusion 21 formed on the inner wall surface of the protective cap 2 contacts with the annular step portion 112 on the outer circumferential surface of the male type connector 1 (see FIGS. 2A to 2C, FIGS. 3A and 3B, and FIGS. 4A to 4C).

By rotating the male type connector 1 relative to the protective cap 2, the guide protrusion 21 slides along the annular step portion 112, so that the guide protrusion 21 faces a position of the axis direction portion 111a of the guide groove 111. With this operation, the male type connector 1 becomes capable of being inserted further into the protective cap 2. From this position, as shown in FIG. 7C, the male type connector 1 is pushed inside, while being rotated clockwise. Accordingly, the guide protrusion 21 slides along the inclined portion 111b of the guide groove 111. With this operation, by a screw action through the engagement between the guide protrusion 21 and the guide groove 111, the male type connector 1 is pulled into the innermost part of the protective cap 2. By rotating further, the guide protrusion 21 enters into the circumferential portion 111c, and goes further beyond the locking convex stripe 111d to reach the trailing end portion 111e. As a result, by the engagement between the guide protrusion 21 and the trailing end portion 111e, the protective cap 2 and the male type connector 1 are combined so as not to separate from each other in the axis direction.

During this operation, the engaging legs 31 of the inner cap 3 enter into the concavity 101 in the front end portion 10 of the male type connector 1. Since the inner cap 3 is retained by the retaining detent 22 of the protective cap 2, the engaging convexities 33 of the engaging legs 31 slide on the inner circumferential surface of the front end portion 10 of the male type connector 1. Finally, as shown in FIG. 7D, the engaging convexities 33 engage with the engaging holes 102 of the male type connector 1, thus establishing the connection. In this state, the disinfecting sponge 34 supported in the inner cap 3 disinfects the front end portion of the male type connector 1. In addition, since an inner circumferential surface at the open end of the protective cap 2 contacts with the O ring 14a, the liquid-tightness inside the protective cap 2 can be maintained and the front end of the male type connector 1 can be protected from the air.

From the state shown in FIG. 7D, by rotating the protective cap 2 relative to the male type connector 1 opposite to the direction for the connection, the inner cap 3 rotates with respect to the protective cap 2 together with the male type connector 1 by the engagement between the engaging convexities 33 and the engaging holes 102 of the male type connector 1. With this rotation, the guide protrusion 21 of the protective cap 2 slides along the guide groove 111 and reaches the axis direction portion 111a. From this state, by separating the male type connector 1 from the protective cap 2 in the axis direction, the male type connector 1 is removed from the protective cap 2 while the inner cap 3 is fitted with the front end of the male type connector 1 so as to assume a state shown in FIG. 7E.

Next, the operation for connecting the male type connector 1 and the female type connector 4 will be described below with reference to FIGS. 8A to 8E. For the details of the structures of the male type connector 1, the inner cap 3, and the female type connector 4, see FIGS. 2A to 2C, FIGS. 4A to 4C, and FIGS. 6A and 6B, respectively.

FIGS. 8A to 8D show states at respective angular positions during an operation in which the female type connector 4 is rotated while the male type connector 1 is fixed in the same angle as shown in FIG. 7E. The female type connector 4 of FIG. 8A is illustrated in the angle of FIGS. 6A and 6B. By rotating the female type connector 4 by 90° clockwise when viewed from the side of the internal end portion 41b, the state of FIG. 8D is obtained. FIG. 8E shows a state where the male type connector 1 is rotated by 90° counterclockwise when viewed from the side of the tube connecting portion 121 from the state shown in FIG. 8D.

Firstly, as shown in FIG. 8A, the male type connector 1 and the female type connector 4 are opposed to each other. In this state, the inner cap 3 is fitted with the front end of the male type connector 1. Next, as shown in FIG. 8B, the male type connector 1 is inserted into the outer cylinder 40 of the female type connector 4. In this operation, the guide protrusion 43 formed on the inner wall surface of the female type connector 4 contacts with the annular step portion 112 on the outer circumferential surface of the male type connector 1. The female type connector 4 is rotated properly so that the guide protrusion 43 faces the axis direction portion 111a of the guide groove 111 of the male type connector 1, whereby the male type connector 1 becomes capable of being inserted further into the female type connector 4. Since the engaging legs 31 of the inner cap 3 are located in the concavity 101 in the front end portion 10 of the male type connector 1, the engaging legs 31 do not protrude from the outer circumferential surface of the male type connector 1. Therefore, when the male type connector 1 is inserted into the outer cylinder 40 of the female type connector 4, less interference occurs with the inner wall surface of the outer cylinder 40, so that a smooth inserting or rotating operation can be realized.

In order to insert the male type connector 1 into an inside, the male type connector 1 is pushed inward, while rotating the female type connector 4 clockwise. With this operation, the guide protrusion 43 slides along the inclined portion 111b of the guide groove 111. According to a screw action generated between the guide protrusion 43 and the guide groove 111, the male type connector 1 reaches the innermost part of the female type connector 4 as shown in FIG. 8C. In this state, the protrusions 32 of the inner cap 3 that is fitted with the front end portion of the male type connector 1 are located on the right side of the inclined portion 44a of the guide step portion 44 shown in FIG. 6A in the circumferential direction.

By rotating further, the guide protrusion 43 enters into the circumferential portion 111c. During the process of the guide protrusion 43 sliding along the circumferential portion 111c, the protrusions 32 provided in the annular portion 30 of the inner cap 3 contact with the inclined portion 44a. By the rotational force exerted through the contact between the side surfaces of the engaging legs 31 and the blocking protrusions 103 of the male type connector 1, the protrusions 32 slide along the inclined portion 44a. Thereby, the inner cap 3 receives a force in the axis direction toward an inside of the female type connector 4 from the inclined portion 44a. As a result, as shown in FIG. 8D, the engagement between the engaging convexities 33 formed at the engaging legs 31 of the inner cap 3 and the engaging holes 102 of the male type connector 1 is released. Finally, the protrusions 32 of the inner cap 3 reach the horizontal step portion 44b of the guide step portion 44 of the female type connector 4. The inner cap 3 is retained in the female type connector 4 in this state. That is to say, when the male type connector 1 is rotated counterclockwise as described later to release the connection between the male type connector 1 and the female type connector 4, the inner cap 3 is not rotated because the engagement between the engaging holes 102 and the engaging convexities 33 has been released. Moreover, since the protrusions 32 of the inner cap 3 and the horizontal step portion 44b are engaged, the inner cap 3 does not move in the axis direction so as to be detached from the female type connector 4.

In addition, when the female type connector 4 and the male type connector 1 are connected as described above, the internal end portion 41b of the inner cylinder 41 of the female type connector 4 pushes and expands the slit in the disinfecting sponge 32 in the inner cap 3 and the slit in the septum 13 supported in the front end portion 10 of the male type connector 1 so as to penetrate through the male type connector 1, whereby the channel is opened. In this process, the inner cylinder 41 of the female type connector 4 is disinfected by the disinfecting sponge 32.

When the connection between the female type connector 4 and the male type connector 1 is released, the male type connector 1 is rotated counterclockwise. With this operation, the engagement between the guide protrusion 43 and the guide groove 111 is released, and therefore both connectors can be separated in the axis direction. In this operation, as described above, the inner cap 3 is left in the female type connector 4 (FIG. 8E).

After that, by fitting a newly-prepared protective cap 2 with the male type connector 1, a new inner cap 3 is fitted with the front end of the male type connector 1, whereby as stated above the front end portion of the male type connector 1 continues to be disinfected.

INDUSTRIAL APPLICABILITY

According to the medical connector system of the present invention, the disinfectant-impregnated member in the inner cap prevents the contamination of the front end portion of the male type connector. Further, every time the protective cap is exchanged, the inner cap is exchanged into a new one, and therefore this system can be disinfected by a new disinfectant-impregnated member at times without a complicated procedure. Therefore, this system is suitable as a connector for connecting a channel for peritoneal dialysis, infusion, and the like.

The invention claimed is:

1. A medical connector system comprising:
a male type connector including a tube connecting portion at a rear end portion of the male type connector;
a protective cap having a substantially cylindrical shape with a closed end and being capable of connecting and disconnecting with/from a front end side of the male type connector;
an inner cap including an annular portion that supports a disinfectant-impregnated member in the annular portion, the inner cap being retained inside the protective cap in an initial state; and
a female type connector having a double-cylinder structure in which an inner cylinder is fixed at one end portion of an outer cylinder, the inner cylinder including an internal end portion located inside the outer cylinder and an external end portion that is exposed outside the outer cylinder and is capable of connecting with a tube,
wherein the inner cap includes a plurality of engaging legs extending from the annular portion in a direction along an axis of the annular portion,
an engaging convexity is formed on an outer surface of a front end portion of each of the engaging legs,
the front end portion of the male type connector has a cylindrical shape and includes engaging concavities so as to allow the engaging convexities at the engaging legs to engage with the engaging concavities from inside,
an inner cap retaining portion is formed on an inner wall surface of the protective cap, and
a force exerted by the engagement between the engaging convexity of the inner cap and the engaging concavity of the male type connector is larger than a force exerted by the inner cap retaining portion to retain the inner cap,
when the protective cap with the inner cap retained in the protective cap is fitted with the male type connector, the engaging convexities at the engaging legs engage with the engaging concavities of the male type connector,
when the protective cap is removed from the male type connector, the inner cap is retained at the front end of the male type connector and is detached from the protective cap, and
when the male type connector with the inner cap retained in the male type connector is connected with the female type connector, the internal end portion of the inner cylinder penetrates through the disinfectant-impregnated member, so that a channel is opened.

2. The medical connector system according to claim 1,
wherein the female type connector includes an inner cap retaining portion, and
when the connection between the male type connector and the female type connector is released, the inner cap is retained inside the female type connector by the inner cap retaining portion and is detached from the front end of the male type connector.

3. The medical connector system according to claim 2,
wherein on an outer surface of the male type connector, a circumferential step portion extending in a circumferential direction is formed so that a diameter at the front end side of the male type connector is smaller than that at a base end side, and a guide groove is formed so as to extend from the circumferential step portion toward the base end, the guide groove including an inclined portion that is inclined with respect to an axis of the male type connector,
on the inner wall surface close to an opening end portion of the protective cap, a guide protrusion is formed, and
when the male type connector is inserted from an opening of the protective cap with the guide protrusion of the protective cap facing the guide groove of the male type connector, and then the protective cap and the male type connector are rotated while being urged axially toward each other, the guide protrusion slides along the guide groove, so that the male type connector is pulled into an inside of the protective cap by a driving force resulting from a screw action by the inclined portion of the guide groove, and the engaging convexities of the inner cap engage with the engaging concavities of the male type connector.

4. The medical connector system according to claim 3,
wherein the male type connector includes a blocking protrusion on an inner circumferential surface of the front end portion of the male type connector, which is capable of contacting with a side face portion of the engaging leg of the inner cap when the inner cap is fitted with the male type connector, the outer cylinder of the female type connector includes a guide protrusion formed on an inner wall surface close to an open end portion of the outer cylinder and a guide step portion including an inclined portion that is inclined with respect to an axis of the female type connector, the inner cap includes protrusions on an outer circumferential surface of the annular portion, and when the male type connector with the inner cap retained in the male type connector is inserted from an opening of the female type connector with the guide protrusion of the outer cylinder facing the guide groove of the male type connector, and then the female type connector and the male type connector are rotated while being urged axially toward each other, the guide protrusion slides along the guide groove, so that the male type connector is pulled into an inside of the female type connector by a driving force resulting from a screw action by the inclined portion of the guide groove, and at the same time the protrusions of the annular portion slide along the inclined portion of the guide step portion of the female type connector while rotation of the engaging legs of the inner cap relative to the male type connector is blocked by the blocking protrusion of the male type connector, so that a force in the axis direction acts on the inner cap so as to separate the inner cap from the male type connector, resulting in release of the engagement between the inner cap and the male type connector, and the inner cap assumes a state of being retained by the inner cap retaining portion of the outer cylinder.

5. The medical connector system according to claim 4, wherein the inner cap retaining portion of the female type connector is configured with a horizontal step portion provided continuously at an inside of the inclined portion of the guide step portion, and when the protrusions of the annular portion of the inner cap contact with the horizontal step portion, the inner cap is prevented from moving in the axis direction toward the opening of the outer cylinder so as to be retained in the female type connector.

6. The medical connector system according to claim 4, wherein the inner cap retaining portion of the female type connector is configured by setting dimensions of constituting elements so that portions of the inner wall of the outer cylinder contact with the outer circumferential surface of the annular portion of the inner cap or so that portions of an outer wall of the internal end portion of the inner cylinder contact with an inner circumferential surface of the annular portion of the inner cap, whereby the inner cap is retained by the thus exerted frictional force.

7. The medical connector system according to claim 1, wherein the male type connector includes a septum member at the front end portion of the male type connector for shielding an inner cavity, and when the male type connector with the inner cap retained at the front end of the male type connector is connected with the female type connector, the internal end portion of the inner cylinder penetrates through the disinfectant-impregnated member in the inner cap and the septum member of the male type connector, so that a channel is opened.

8. A protective cap assembled member used in the medical connector system according to claim 1, comprising:

the protective cap having a substantially cylindrical shape with a closed end; and the inner cap retained at an inside of the protective cap and including an annular portion with a disinfectant-impregnated member supported in the annular portion, wherein on an inner wall surface of the protective cap, an inner cap retaining portion for retaining the inner cap is formed, the inner cap includes a plurality of engaging legs extending from a circumferential edge portion of the annular portion in a direction along an axis of the annular portion, and an engaging convexity is formed at a front end of each of the engaging legs so as to protrude outward, and the inner cap is retained in the inner cap retaining portion so that the front ends of the engaging legs are directed toward an opening of the protective cap.

* * * * *